United States Patent [19]

Nason

[11] Patent Number: 5,238,649

[45] Date of Patent: * Aug. 24, 1993

[54] SPECIMEN TEST UNIT

[76] Inventor: Frederic L. Nason, 941 Avenida Acaso, Camarillo, Calif.

[*] Notice: The portion of the term of this patent subsequent to Dec. 18, 2007 has been disclaimed.

[21] Appl. No.: 796,661

[22] Filed: Nov. 25, 1991

Related U.S. Application Data

[63] Continuation-in-part of Ser. No. 625,750, Dec. 10, 1990, Pat. No. 5,078,968, which is a continuation of Ser. No. 153,951, Feb. 9, 1988, Pat. No. 4,978,504.

[51] Int. Cl.$^5$ .............................................. G01N 1/00
[52] U.S. Cl. ............................. 422/58; 128/759; 422/56; 422/61; 422/100; 435/294; 435/295
[58] Field of Search .................. 422/56, 57, 58, 61, 422/100, 101, 102, 294; 435/295, 296, 810; 128/759, 771; 604/1, 2, 3

[56] References Cited

U.S. PATENT DOCUMENTS

| | | | |
|---|---|---|---|
| 2,490,168 | 2/1947 | Strauss | 128/269 |
| 3,163,160 | 11/1962 | Cohen | 128/2 |
| 3,450,129 | 7/1966 | Avery et al. | 128/2 |
| 3,640,268 | 2/1972 | Davis | 128/2 |
| 3,776,220 | 12/1973 | Monaghan | 128/2 |
| 3,792,699 | 2/1974 | Tobin et al. | 128/2 |
| 3,883,396 | 5/1975 | Thomas, Jr. et al. | 435/37 |
| 3,890,204 | 7/1975 | Avery | 128/2 |
| 3,913,564 | 10/1975 | Freshley | 128/2 |
| 3,915,800 | 10/1975 | Horlach | 435/101 |
| 3,918,435 | 11/1975 | Beall et al. | 128/2 |
| 3,923,604 | 12/1975 | Monaghan | 128/2 |
| 3,954,563 | 5/1976 | Mennen | 435/810 |
| 3,980,954 | 6/1975 | Greenspan | 128/2 |
| 4,014,746 | 3/1977 | Greenspan | 128/2 |
| 4,014,748 | 3/1977 | Spinner et al. | 128/2 |
| 4,059,404 | 11/1977 | Schuster et al. | 422/56 |
| 4,175,008 | 11/1979 | White | 435/295 |
| 4,184,483 | 1/1980 | Greenspan | 435/295 |
| 4,196,167 | 4/1980 | Olsen | 422/61 |
| 4,223,093 | 9/1980 | Newman et al. | 435/295 |
| 4,300,910 | 11/1981 | Pannwitz | 422/61 |
| 4,311,792 | 1/1982 | Avery | 435/30 |
| 4,312,950 | 1/1982 | Snyder et al. | 435/295 |
| 4,340,670 | 7/1982 | Joslin et al. | 435/25 |
| 4,355,113 | 10/1982 | Mennen | 422/61 |
| 4,387,725 | 6/1983 | Mull | 128/759 |
| 4,409,988 | 10/1983 | Greenspan | 435/294 |
| 4,562,043 | 12/1985 | Mennen et al. | 435/810 |
| 4,604,360 | 8/1986 | Hounsell | 435/287 |
| 4,635,488 | 1/1987 | Kremer | 422/58 |
| 4,707,450 | 11/1987 | Nason | 422/61 |
| 4,770,853 | 9/1988 | Bernstein | 422/61 |
| 4,813,432 | 3/1989 | Saint-Amand | 128/749 |
| 5,078,968 | 1/1992 | Nason | 422/58 |

FOREIGN PATENT DOCUMENTS 0155747 10/1985 European Pat. Off. .

Primary Examiner—Robert J. Warden
Assistant Examiner—Laura E. Collins
Attorney, Agent, or Firm—Kelly Bauersfeld & Lowry

[57] ABSTRACT

An improved test unit is provided for use in the collection and analysis of biological specimens and the like. The specimen test unit includes a swab member adapted for collection of a specimen to be tested. The test unit incorporates one or more reagents or other test fluids for delivery into contact with the specimen on the swab member. In accordance with various embodiments, the contacted specimen and fluid are then delivered through one or more porous members for analysis and/or to contact an additional reagent or reagents in the course of performing a selected test. In some forms, one or more of the porous members is preimpregnated with a selected reagent or constituent thereof. Moreover, in some forms, one or more of the porous members is formed from a hydrophobic material to serve as a fluid seal until fluid is forced therethrough, for example, by squeezing a reagent-containing housing member of the test unit. In all embodiments, the test unit is substantially self-contained to perform the desired test, with minimal risk of exposing testing personnel to the collected specimen and/or to the various reagents.

24 Claims, 9 Drawing Sheets

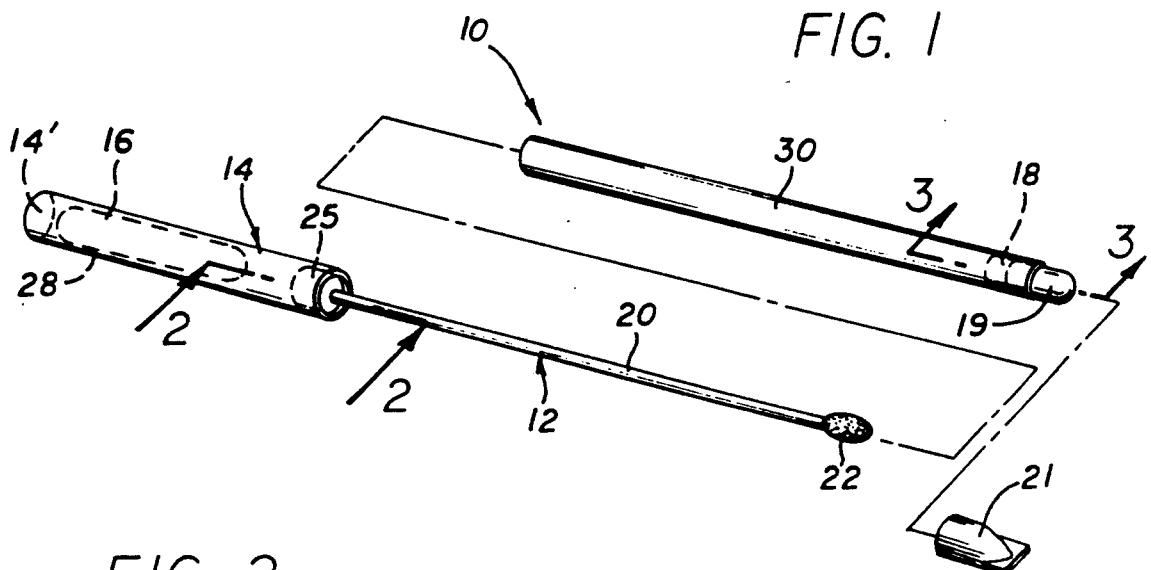

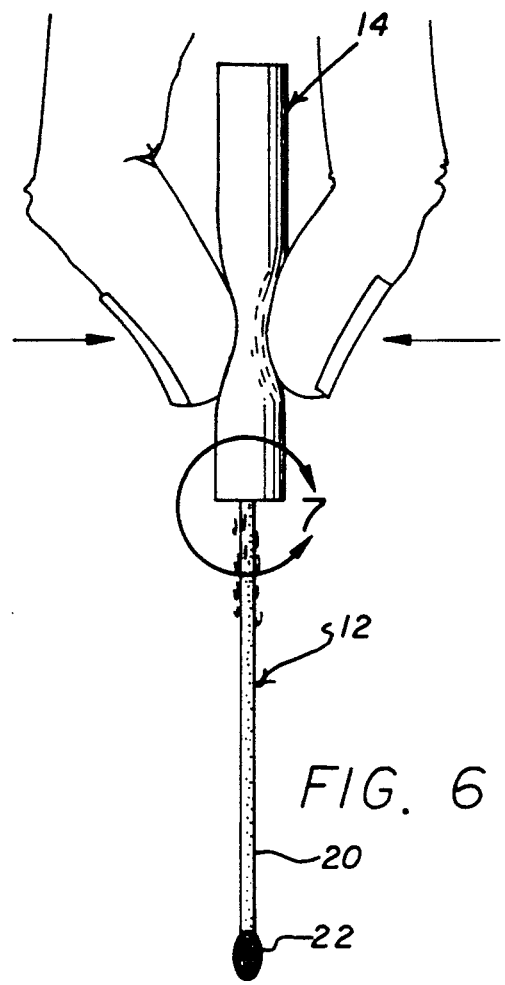
FIG. 6
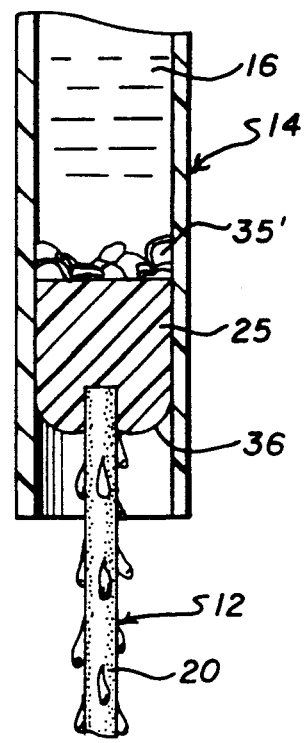
FIG. 7
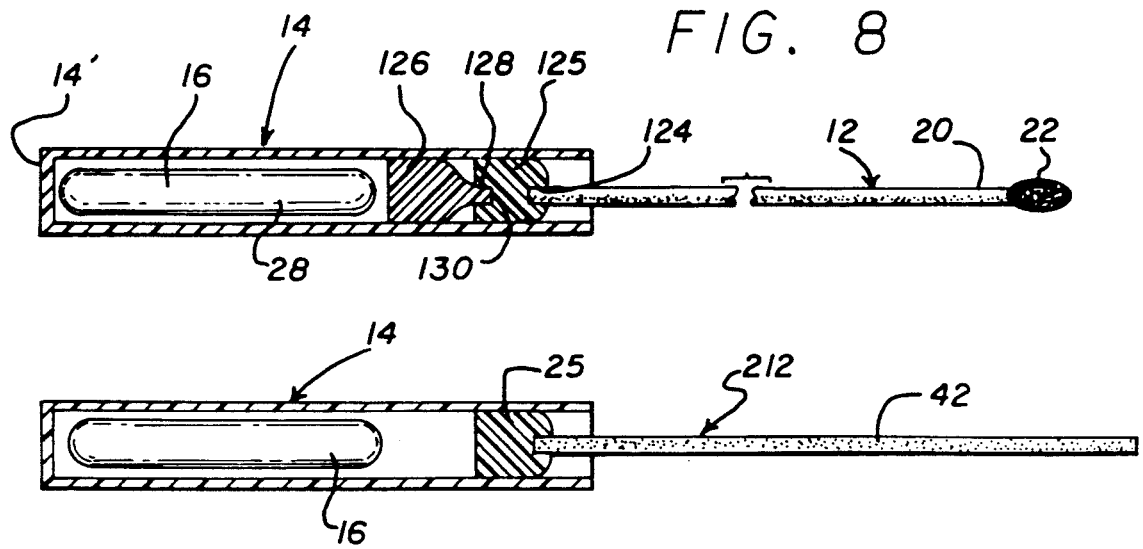
FIG. 8
FIG. 9

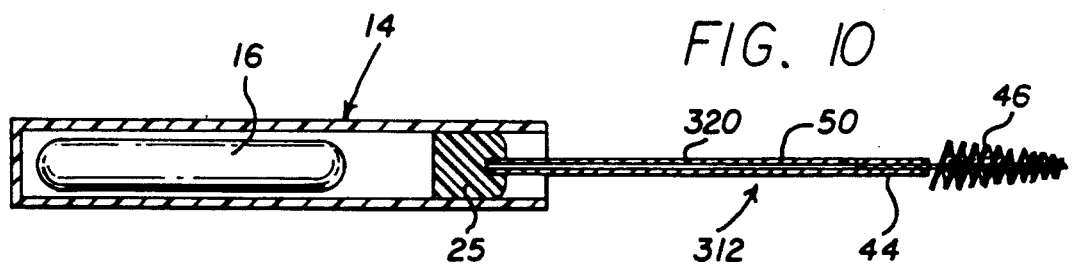
FIG. 10
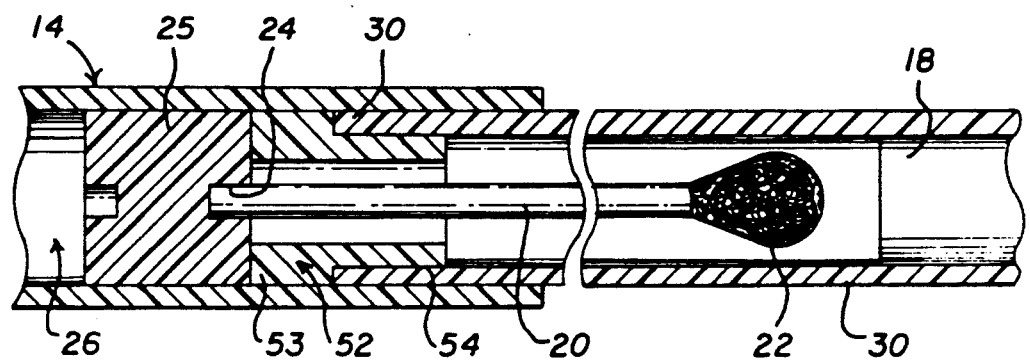
FIG. 11
FIG. 13
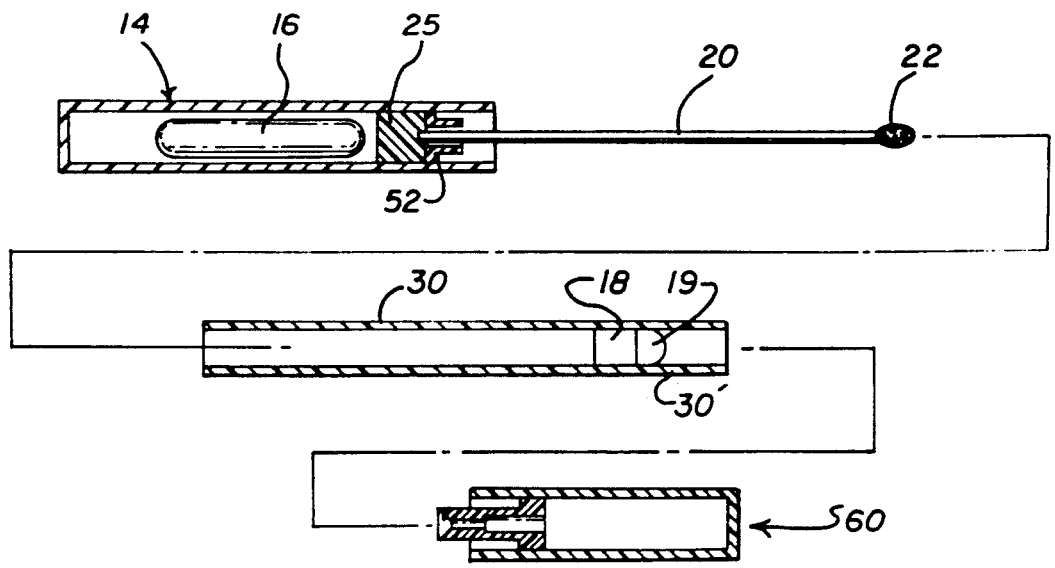

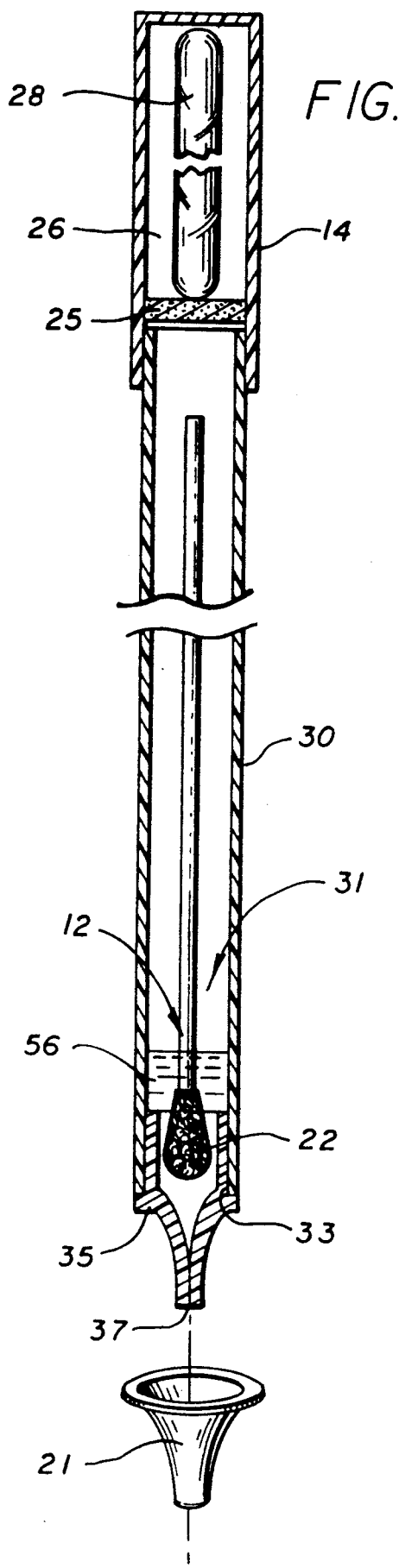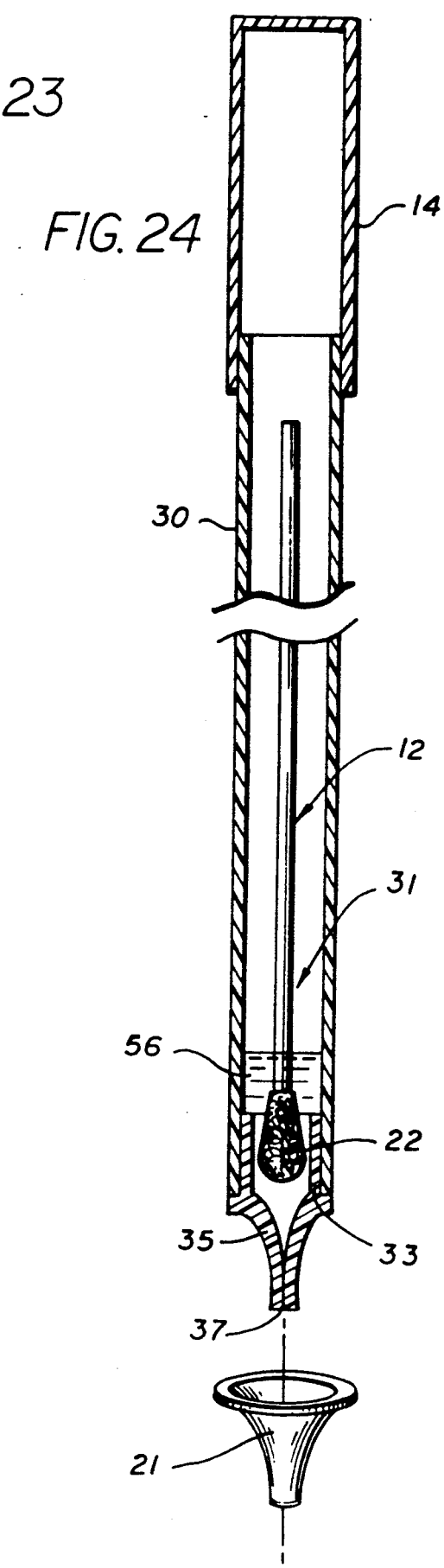

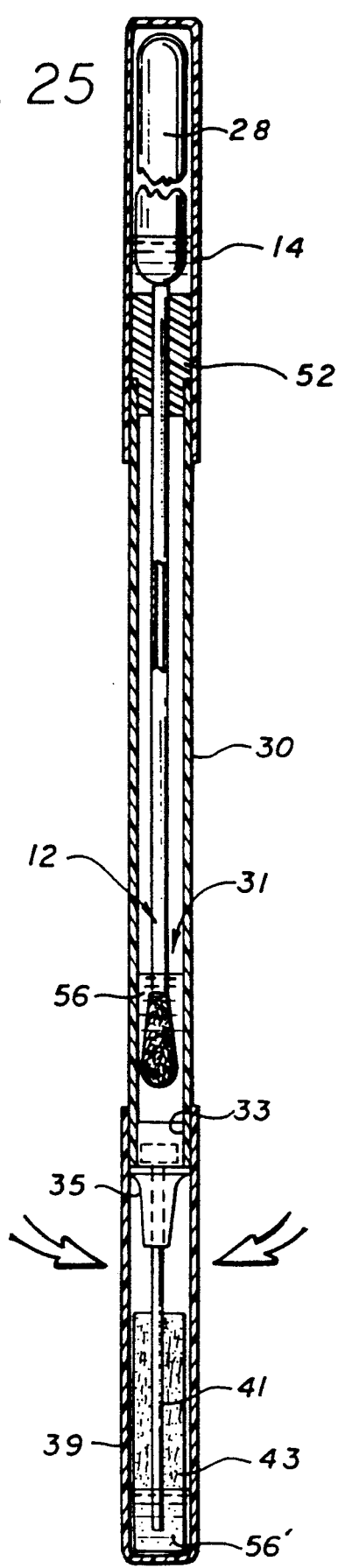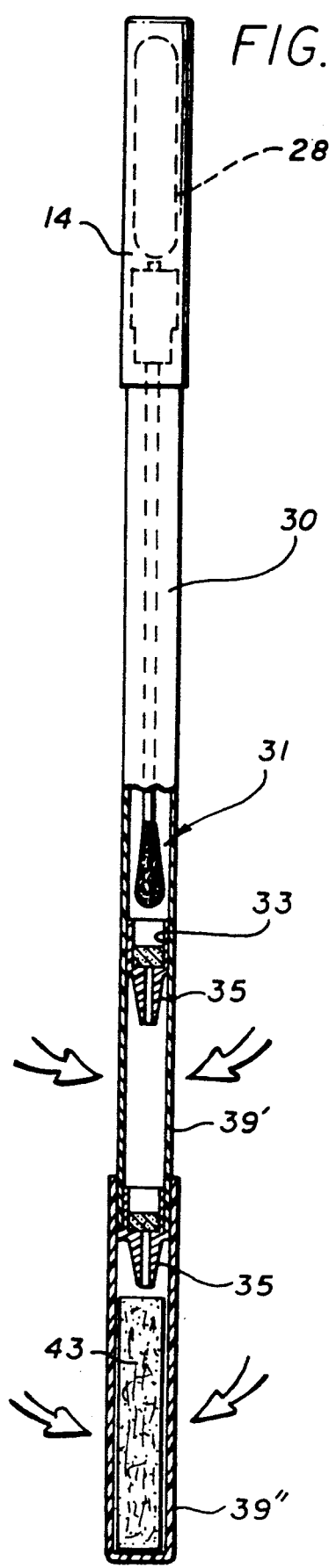

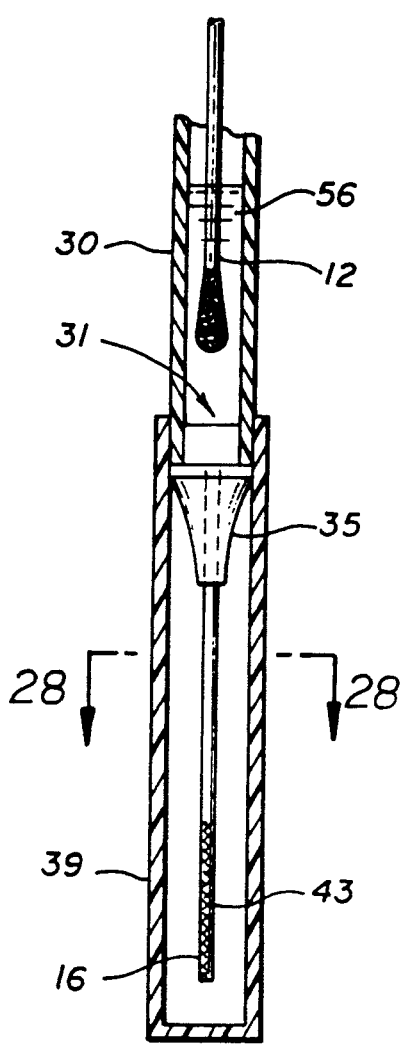
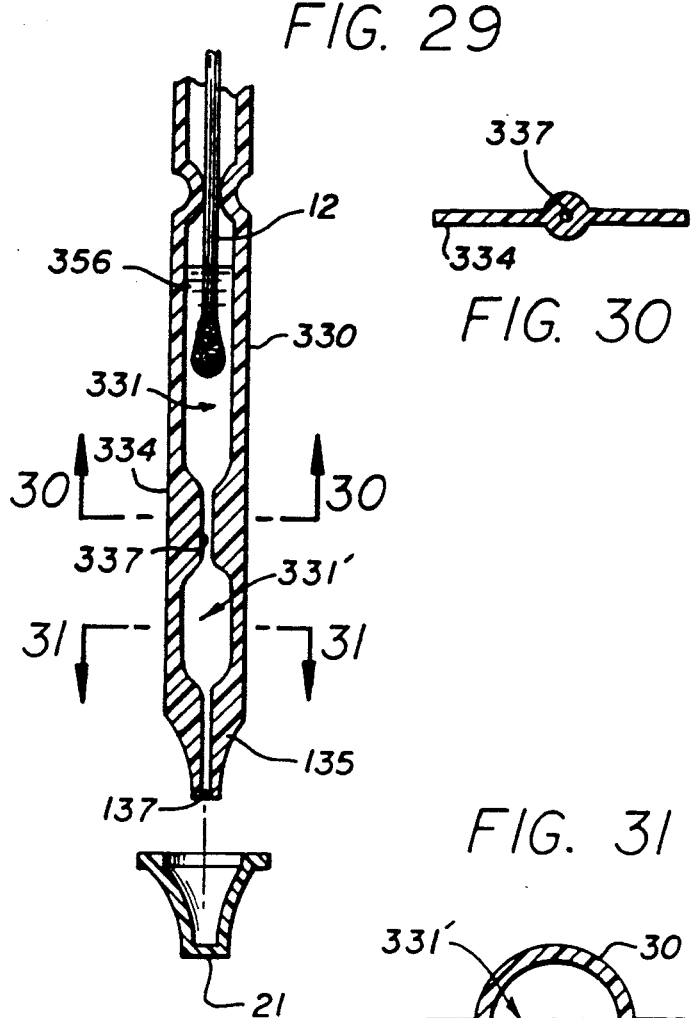
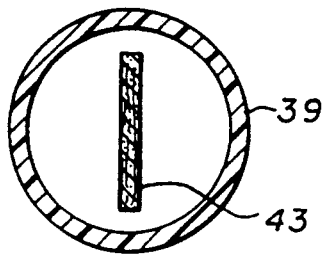
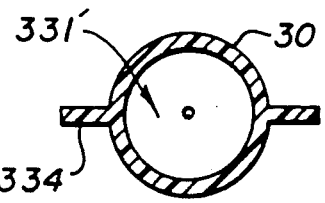
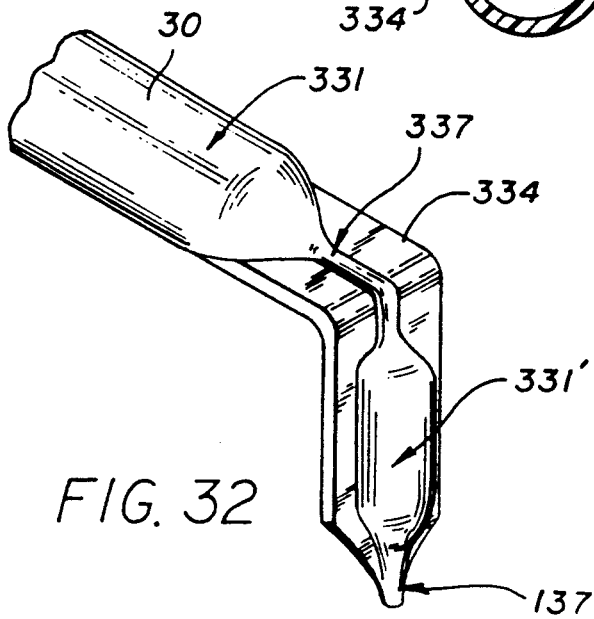

5,238,649

SPECIMEN TEST UNIT

BACKGROUND OF THE INVENTION

This application is a continuation-in-part of copending application Ser. No. 625,759, filed on Dec. 10, 1990, now U.S. Pat. No. 5,078,968 which in turn is a continuation of copending application Ser. No. 153,951 filed on Feb. 9, 1988, now U.S. Pat. No. 4,978,504, issued Dec. 18, 1990.

This invention relates generally to improvements in medical swabs and the like of the type used for collecting biological specimens for purposes of performing a variety of medical tests with respect to those specimens. More particularly, this invention relates to an improved and substantially self-contained swab unit adapted for use with one or more reagents, wherein the swab unit has having improved means for handling the reagents and the specimen in the course of performing medical tests.

Medical swabs in general are well-known in the art for use in collecting biological specimens from a patient for further analysis. Such medical swabs commonly comprise a fibrous swab tip at one end of an elongated stick or shaft which is manually handled to contact the swab tip with selected tissue cells or other biological specimen obtained, for example, from within the ear, nose or throat of a patient. As a result, some of the targeted biological specimen adheres to the swab tip which can then be contacted with one or more selected reagents to indicate, for example, the presence of infection or other information regarding patient condition. The tests commonly performed with such patient specimens include, by way of example, fluorescent tests, enzymatic tests, monoclonal based tests, agglutination tests, etc.

In accordance with standard techniques, the collected biological specimen is normally transferred from the swab tip to a slide or other laboratory apparatus such as a test tube or the like for contact with the selected reagent and further analysis. However, it is frequently difficult to insure transfer of a sufficient specimen quantity from the swab tip to the laboratory slide or the like to insure accurate test results. Moreover, in many instances, the collected specimen must be transported to a medical laboratory for performance of selected assays, but delays between the time of specimen collection and actual test performance can result in partial or complete drying of the specimen, with a corresponding decrease in test reliability.

Various swab collection devices have been proposed in efforts to provide enhanced contact between a specimen and reagent, or, in the alternative, to sustain the specimen during post-collection transport to a medical laboratory or the like. Such swab collection devices have been provided in the form of a compact kit including a fibrous-tipped swab together with one or more reagents for contacting a specimen collected upon the swab. In some designs, the reagent is carried by a frangible glass ampoule which is broken at the appropriate time to release a reagent for contacting the specimen on the swab tip. Other designs have provided reagents within rupturable plastic cells for appropriate release to contact the collected specimen. These prior collection device designs, however, have not provided effective means for filtering particulate such as mucous and other non-fluid debris from a collected specimen, wherein such filtration of the specimen can be a requirement in order to obtain reliable test results. Moreover, these prior devices have not been designed for relatively easy delivery of a mixed specimen and reagent from the device for further analysis, as required in many tests, without exposing testing personnel to unnecessary risks in contacting a collected specimen or the reagents associated therewith.

There exists, therefore, an on-going need for an improved specimen test unit having relatively simple yet effective means for filtering a collected specimen and/or reagent, as required by the specific test to be performed, and/or for easy delivery of mixed specimen and reagent from the test unit to a subsequent convenient site for further analysis. In addition, there exists a need for an improved test unit designed for handling a collected specimen and associated reagents safely without risk of contact by testing personnel. The present invention fulfills these needs and provides further related advantages.

SUMMARY OF THE INVENTION

In accordance with the invention, an improved specimen test unit is provided for use in collecting a biological specimen or the like, for example, from a patient. The invention includes relatively simple and efficient apparatus for applying one or more selected reagents into direct contact with the collected specimen for purposes of performing a selected medical assay. Delivery means which may include a filter is provided for delivering the mixed specimen and reagents for further analysis in accordance with the requirements of the test to be conducted.

In accordance with a preferred form of the invention, the specimen test unit comprises a specimen collecting means such as an elongated swab member adapted for use in collecting a biological specimen, for example, by directly contacting a portion of the swab member with selected patient tissue, cells, fluids, etc. The swab member with the collected specimen thereon is placed into a specimen chamber defined by a pair of housing members of open-ended cylindrical shape or the like and adapted to interfit with each other. When the housing members are interfitted, they define the specimen chamber having a size and shape to enclose and contain the swab member with specimen collected thereon. In one form, the swab member can be provided as a separate element disconnected from the housing members and adapted for loose placement into the specimen chamber after specimen collection. In another form, the swab member can be physically connected to and supported by one of the housing members in a manner and position for swab member placement into the specimen chamber when the two housing members are interconnected.

The collection specimen on the swab member is placed into the specimen chamber with at least one reagent for contact between the specimen and reagent. In one simplified form, the reagent can be separately added to the specimen chamber at the time of specimen collection and swab member placement into the specimen chamber, before the specimen chamber is closed by interfitting the two housing members. In other forms, the one or more reagents can be carried by at least one of the housing members within a separate reagent chamber for delivery to the specimen chamber after the two housing members are interfitted to enclose the swab member with specimen thereon.

For example, at least one reagent can be carried within one housing member formed from resilient plastic or the like, wherein the reagent is normally separated from the specimen chamber by a valve device, such as a porous plug having flow passages formed therein of a sufficiently small size to prevent reagent flow therethrough unless said one housing member is manually squeezed to pressure-force the reagent through the plug from the reagent chamber to the specimen chamber. For added reagent confinement prior to use, the reagent may additionally be contained within a frangible ampoule disposed within the reagent chamber wherein the ampoule can be fractured by deforming said one housing member to release the reagent.

In some forms of the invention, the porous plug is preimpregnated with a selected reagent, for example, by presoaking the plug with a reagent and drying that reagent within the plug prior to plug assembly with said one housing member. Alternately, multiple porous plugs impregnated with different reagents can be mounted end-to-end within said one housing member, resulting in serial reagent contact with a selected test fluid forced through the filter plugs upon squeezing of the housing member. Such end-to-end plugs are beneficially contoured to insure serial fluid flow therethrough. Moreover, any one of the plugs may be constructed with hydrophobic or nonwettable characteristics to define an effective liquid seal preventing test fluid passage until the test fluid is pressure-forced therethrough by squeezing of said one housing member.

In accordance with other preferred aspects of the invention, the other or second housing member defines an outlet port leading from the specimen chamber to the exterior. In one form, the outlet port has an occluding member mounted therein to normally prevent flow of the mixed specimen and reagent from the specimen chamber. In this regard, the occluding member has at least one small flow passage formed therein of a sufficiently small size to prevent unpressurized or unforced liquid outflow from the specimen chamber. However, the flow passage will permit pressurized or forced liquid outflow from the specimen chamber to the exterior. In one form, pressure-forced outflow is achieved by manually squeezing one or both housing members to increase the pressure within the specimen chamber and thereby force some of the mixed specimen and reagent to flow through the occluding member to the exterior for future testing and analysis. In another form, an auxiliary housing member can be mounted onto the second housing member at a position enclosing the outlet port, wherein the auxiliary housing member is adapted for manual squeezing and release to provide a vacuum-drawn pressure differential which effectively draws a portion of the mixed specimen and reagent from the specimen chamber.

The auxiliary housing member may include one or more elongated porous wick elements for controlled capillary fluid flow of the mixed specimen and reagent. The wick element or elements may be impregnated with additional reagents in accordance with the medical assay to be performed. The wick elements serve as time flow control meters to provide an automated incubation and/or holding time with respect to a particular test, and to permit controlled outflow of mixed specimen and reagent without requiring housing member deformation.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating one preferred construction for the specimen test unit embodying the novel features of the invention;

FIG. 2 is an enlarged fragmented sectional view taken generally on the line 2—2 of FIG. 1;

FIG. 3 is an enlarged fragmented vertical sectional view taken generally on the line 3—3 of FIG. 1;

FIG. 4 is a somewhat diagrammatic view illustrating use of the invention in the collection of a biological specimen;

FIG. 5 is a perspective view illustrating a step in releasing a reagent carried by the test unit;

FIG. 6 is an enlarged elevational view depicting filtered transfer of a released reagent to a swab member for direct contact with a collected biological specimen thereon;

FIG. 7 is an enlarged fragmented vertical sectional view corresponding generally with the encircled region 7 of FIG. 6;

FIG. 8 is a fragmented longitudinal sectional view illustrating one alternative preferred form of the invention;

FIG. 9 is a longitudinal sectional view illustrating another alternative preferred form of the invention;

FIG. 10 is a longitudinal sectional view depicting still another alternative preferred form of the invention;

FIG. 11 is an enlarged fragmented sectional view showing a further alternative construction for the invention, including a sealing cap for use in combination with the test unit;

FIG. 13 is an exploded sectional view showing the test unit for use in combination with a further modified sealing cap and auxiliary dropper cartridge;

FIG. 23 is an exploded vertical sectional view illustrating another alternative preferred form of the invention;

FIG. 24 is an exploded vertical sectional view of a still further alternative embodiment of the invention;

FIG. 25 is another vertical sectional view of an alternative form of the invention, depicting an auxiliary housing member for receiving mixed specimen and reagent from a specimen chamber;

FIG. 26 is a vertical sectional view similar to FIG. 25, but showing a further modified form of the invention to include multiple auxiliary housing members;

FIG. 27 is an enlarged and fragmented vertical sectional view depicting another modified form of the invention;

FIG. 28 is an enlarged transverse sectional view taken generally on the line 28—28 of FIG. 27;

FIG. 29 is an enlarged fragmented vertical sectional view illustrating a further alternative embodiment of the invention;

FIG. 30 is an enlarged transverse sectional view taken generally on the line 30—30 of FIG. 29;

FIG. 31 is an enlarged transverse sectional view taken generally on the line 31—31 of FIG. 29; and FIG. 32 is a fragmented perspective view showing deformation of the embodiment of FIGS. 29-31 to facilitate delivery of mixed specimen and reagent therefrom.

DETAILED DESCRIPTION OF THE PREFERRED EMBODIMENTS

Figure 12:
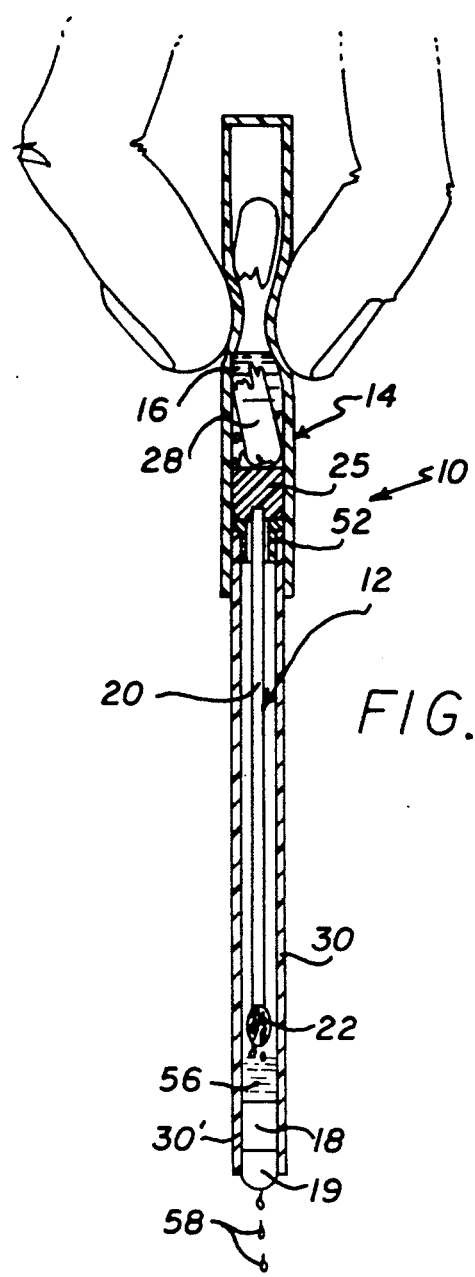
FIG. 12 is a vertical sectional view showing use of the embodiment of FIG. 11.

As shown in the exemplary drawings, an improved specimen test unit, referred to generally in FIG. 1 by the reference numeral 10, is provided for use in collecting a biological specimen or the like and for performing a selected test, such as a medical assay, with respect to the collected specimen. The test unit 10 comprises the combination of a swab member 12 projecting from an enlarged housing member or base 14 having one or more reagents 16 or other test fluid encased therein. At least one porous plug or occluding member, such as a pair of filter members 18 and 19 are incorporated into the test unit 10 for initially retaining the reagent and/or the specimen within a specimen chamber, and for thereafter permitting flow through passage of the mixed specimen and reagent to an external site for further test and analysis as required for the selected test, and in a manner to be described in more detail herein.

The improved specimen test unit 10 of the present invention provides a relatively simple and self-contained product for collecting and testing biological specimens such as tissue, cells, body fluid, and the like obtained from a patient. The test unit provides means for substantial and thorough contact of the collected specimen with one or more selected reagents, without requiring additional test apparatus such as laboratory slides, test tubes, etc. A wide variety of selected tests may be performed and the results read directly at a selected location within the test unit, after which the entire test unit may discarded as a disposable item. Alternately, the specimen and associated test fluid can be delivered safely and efficiently from the test unit 10 for further laboratory analysis or the like, without subjecting test personnel or others to unnecessary exposure to the specimen or associated reagents. Importantly, in some embodiments, the test unit 10 incorporates relatively simple yet highly effective filter means to provide appropriate fluid filtering at various stages within the test unit, as may be required by the particular test to be performed. Examples of tests in which the test unit 10 may be used include, but are not limited to, fluorescent tests, enzymatic tests, monoclonal based tests, agglutination tests, and the like.

As shown in detail in FIGS. 1-7, with respect to one preferred form of the invention, the specimen test unit 10 constitutes an elongated, relatively thin implement having an overall size and shape for easy manual handling during use. More specifically, the test unit 10 comprises the swab member 12 shown in FIG. 1 in the form of an elongated shank or shaft 20 supporting a swab tip 22 of cotton, Dacron or other absorbent fibrous material which is wound or otherwise suitably attached to the forward end of the shank 20. The shank 20 is formed from a plastic or other suitable material to have a relatively stiff but somewhat flexible construction corresponding generally with the construction of conventional swabs used in a medical environment.

The rear end of the swab shank 20 may be seated within a shallow counterbore 24 formed in a porous plug or filter member 25, wherein the filter member is mounted in turn within the base 14 for the test unit 10. As shown best in FIGS. 1 and 2, the base 14 has a generally cylindrical hollow construction with a closed rear end wall 14' and an open front end for relatively snug-fit slide-in reception of the filter member 25. The filter member 25 cooperates with the base 14 to define a substantially closed reagent chamber 26 for containing at least one reagent, such as the reagent 16 encased initially within a frangible glass ampoule 28.

A cylindrical cap 30 is provided as part of the specimen test unit 10 and has a rearwardly open construction to fit over the swab member 12 in seated relation extending partially into the open front end of the base 14. In this regard, the base 14 and the cap 30 constitute a pair of open-ended tubular housing members adapted for slide-fit interconnection to cooperatively define a chamber for receiving and protecting the swab member 12, including the shank 20 and the swab tip 22, thereby permitting the test unit 10 to be supplied with the swab 12 initially in a closed sterile condition. In this regard, the filter member 25 is slightly inset into the front end of the base 14 (FIG. 2) to accommodate slide-in reception of the cap rear end. Alternately, the cap rear end can be sized for sliding fit over the front end of the base 14, or any other suitable connection.

When performance of a medical test is desired, the cap 30 is removed quickly and easily from the base 14 to expose the swab member 12 for use in collecting the medical specimen. More specifically, as shown generally in FIG. 4, the test unit 10 can be manually handled to move the swab tip 22 into contact with and to collect tissues or cells or other biological materials 32 which may be present, for example, within the throat 34 of a patient. Alternately, a wide variety of other types of biological or other specimens may be collected in accordance with the tests or analyses to be performed. Conveniently, the swab shank 20 is normally provided with sufficient bending capability to accommodate specimen collection while also providing sufficient rigidity to permit the swab tip 22 to be pressed or scraped against the tissues or cells during specimen collection.

Once the specimen has been collected on the swab tip 22, the cylindrical base 14 of the test unit 10 can be bent or squeezed or otherwise deformed to fracture the reagent-containing ampoule 28 within the reagent chamber 26. To this end, the base 14 is constructed from a plastic or the like having sufficient flexibility to accommodate this deformation and then return elastically substantially to the initial nondeformed state. When the ampoule 28 is fractured, as viewed in FIG. 5, the reagent 16 therein is released for delivery to the collected specimen at the swab tip 22. This delivery is achieved by manually pressing the side walls of the base 14, as viewed in FIG. 6, to increase the pressure within the reagent chamber 26 sufficiently to drive or force the liquid reagent through the open porous structure of the filter member 25, as viewed in FIGS. 6 and 7. During this reagent delivery step, the test unit 10 is normally oriented in a substantially vertical position causing the reagent to drain downwardly along the shank 20 into direct contact with the swab tip 22 and the specimen collected thereon.

The porous filter member 25 advantageously separates the reagent 16 from glass particles and fragments 35' (FIG. 7) remaining within the base 14 upon ampoule fracture. Accordingly, the glass particles and fragments 35' do not drain along the swab shank 20 and do not contact the swab tip 22, whereby the glass fragments do not interfere with performance of the selected test and do not pose a safety hazard. In this regard, the preferred filter member 25 is formed as a molded plastic filter plug material such as a blown polyethylene plastic or resin or the like having a controlled porosity typically for filtering particles to a size within the range of about 3 to about 10 microns. Such filter plugs are commercially available, for example, from Porex Technologies of Fairburn, Va., or from Chromex Corporation of Brooklyn, N.Y. In addition, to insure reagent flow onto the swab shank 20 for drainage to the swab tip 22, when the test unit 10 is vertically oriented as viewed in FIGS. 6 and 7, the front nose 36 of the plug 25 is rounded (FIG. 7) to define a generally outwardly presented convex surface which guides reagent flow onto the shank 20. This step of delivering the reagent to the swab tip 22 may be performed with the cylindrical cap 30 held loosely about the swab member 12, whereby the cap 30 can be used to collect excess reagent dripping from the swab tip 22. Alternately, as will be described with respect to FIG. 12, the reagent delivery occurs in the preferred form with the cap 30 interfitted with the base 14.

In accordance with various specific test applications, the ampoule 28 within the base 14 may contain a wetting solution such as water, saline solution, etc., in accordance with the requirements of the selected test. In this instance, the filter member 25 can be preimpregnated with a selected reagent, for example, by presoaking the plug 25 with a selected reagent which is allowed to dry prior to plug installation into the base 14. Subsequent delivery of the wetting agent through the plug 25 returns the dried reagent to solution form for transfer along the swab shank 20 to the swab tip, in the same manner as previously described.

Several alternative embodiments of the swab member of the test unit are shown generally in FIGS. 8-11, wherein components identical to those depicted in FIGS. 1-7 are referred to by the same reference numerals. More particularly, as shown in FIG. 8, a cylindrical base 14 contains a reagent 16 within a frangible ampoule 28 or the like, but in this embodiment, multiple porous plug members 125 and 126 are provided for series passage of the reagent 16 or other test fluid within the base 14. More particularly, a first porous plug member 125 is received into the front end of the base 14 and includes a shallow front counterbore 124 for seated reception of the shank 20 of the swab member 12. However, this first plug member 125 additionally has a shallow counterbore 128 in the rear face thereof for snap-fit or press-fit reception or the like of a tapered nose 130 of the second porous plug member 126. Both of these plug members 125 and 126 can be preimpregnated with different reagents for series contact with the reagent 16 or other test fluid when that test fluid is expressed from the base 14. Moreover, the second plug member 126 can be formed from a sufficiently hydrophobic material to provide an effective liquid seal unless and until the base 14 is squeezed to express the reagent 16. Conveniently, the contoured or tapered nose 130 of the second plug member 126 assures test fluid passage serially through the first member 125, rather than by leakage around the first filter member 125. Moreover, both plug members 125 and 126 may be conveniently constructed as porous filter plugs similar to the filter plug 25 shown in FIGS. 1-7.

In the embodiment shown in FIG. 9, a simplified swab member 212 is shown in the form of an absorbent rod 42 projecting forwardly from the porous plug member 25 at the front end of a base 14. In this version, the absorbent rod 42 can be used to collect a specimen thereon at any convenient position along the length of the rod, after which the reagent 16 or other test fluid can be expressed to the rod in the same manner as previously described. However, the reagent not only drains along the rod but also wicks thereinto for purposes of contacting the collected specimen. Of course, if desired, one or more porous plug members having reagents preimpregnated therein may be used, with multiple plug members being adapted for serial test fluid passage, as viewed in FIG. 8.

A further alternative embodiment of the invention is shown in FIG. 10, wherein a further modified swab member 312 includes a hollow swab shank 320 having a rear end anchored into the porous plug member 25. In this version, the forward end of the swab shank 320 receives a short mounting stem 44 of a brush 46 having bristles for collection of the desired specimen. The reagent 16 is expressed through the plug member 25 for flow through and about the swab shank 320 into contact with the brush bristles, in generally the same manner as previously described with respect to FIGS. 1-7. However, reagent flowing through the swab shank interior is permitted to discharge therefrom through a small port 50 near the shank front end for subsequent flow to the brush bristles 46. Multiple filter members adapted for serial test fluid passage may again be provided, if desired.

FIG. 11 illustrates still another alternative configuration of the invention to include a cap seal ring 52 within the base 14 for sealing engagement with the cap 30, thereby insuring sterility of the product prior to use. In this embodiment, the base 14 again has an open front end for snug, slide-fit reception of the porous filter member 25 having the shallow counterbore 24 in the front face or nose thereof to receive and anchor the rear end of the swab member 12. Of course, any of the various swab members shown in FIGS. 1-7 can be used. The seal ring 52 is also seated into the front end of the base 14 and includes a cylindrical seat 53 abutting against the forwardmost face of the porous plug member 25. This seat 53 is received tightly into the base 14 and is joined to a forwardly projecting annular lip 54 of reduced diametric size. The lip 54 cooperates with the interior surface of the housing member 14 to define a forwardly open annular recess for snug, substantially sealed reception of the rearmost edge of the cylindrical cap 30. Accordingly, the seal ring 52 and the cap 30 cooperate to define a high quality seal maintaining the sterility of the swab member 12 at least until the cap is removed.

Regardless of the particular selected configuration of the swab member, as described in FIGS. 1–11, the collected specimen can be contacted by and mixed with the test fluid including the reagent or reagents to form a liquid pool 56 at the bottom of the cylindrical cap 30, as viewed in FIG. 12. In this arrangement, the swab member is utilized as previously described to collect a selected biological specimen, followed by placement of the swab member 12 (FIG. 12) into the enclosed specimen chamber defined by interfitting connection of the base 14 and the cap 30. With the swab member and collected specimen disposed in the specimen chamber, the reagent can then be delivered quickly and easily to the specimen chamber by fracturing the ampoule 28 and then squeezing the base 14 sufficiently to increase the pressure level within the reagent chamber 26 and thereby deliver the reagent through the porous plug member 25 to the specimen chamber.

The lower or outboard end 30' of the cylindrical cap 30 defines an open outlet port which is closed or effectively occluded to normally prevent fluid flow therethrough, by means of a porous member defining at least one flow path of a sufficiently small size to prevent unforced liquid flow. FIG. 12 shows this porous member in the form of at least one porous plug or filter member, such as the serially mounted pair of filter members 18 and 19 shown in the drawings. A small end cap 21 (FIG. 1) may also be provided to enclose and cover the filter members 18 and 19 and associated outlet port prior to use of the test unit. The lowermost filter member 19 protrudes a short distance from the cap 30 and terminates in a rounded contour, such as the hemispherical contour shown in the drawings. Both filter plugs 18 and 19 may, if desired, be preimpregnated with selected reagents, and one or both of the filter plugs 18 and 19 may have hydrophobic characteristics to define an effective fluid seal which normally prevents fluid leakage from the within the cap 30.

The mixed specimen and reagent pool 56 within the cap 30 can be expressed through the filter members 18 and 19 for performance of further tests. More particularly, as viewed in FIG. 12, the cap 30 remains secured onto the base 14 with its upper or open end in substantially sealed relation with the housing member. In this configuration, the base 14 and/or the cap 30 can be squeezed again to express a portion of the mixed reagent and specimen 56 through the filter plugs 18 and 19. Such expression of the fluid beneficially filters the specimen and/or reagent, and further functions to contact the specimen with any additional reagents carried by the filter members 18 and 19. The rounded front contour of the filter plug 19 advantageously insures formation of discrete droplets 58 of mixed reagent and specimen which can be subjected to further testing, for example, by placement onto a slide or the like (not shown in FIG. 12) for further laboratory analysis. Importantly, however, in addition to permitting a portion of the mixed specimen and reagent to flow from the specimen chamber to the exterior of the test unit, the porous occluding member or members at the outlet port normally prevent such outflow during an initial contact period between the specimens and reagent.

Figure 14:
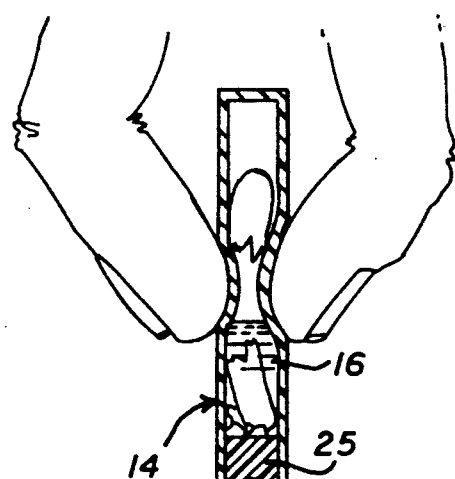
FIG. 14 is an enlarged fragmented sectional view illustrating use of the embodiment of FIG. 13.
Figure 15:
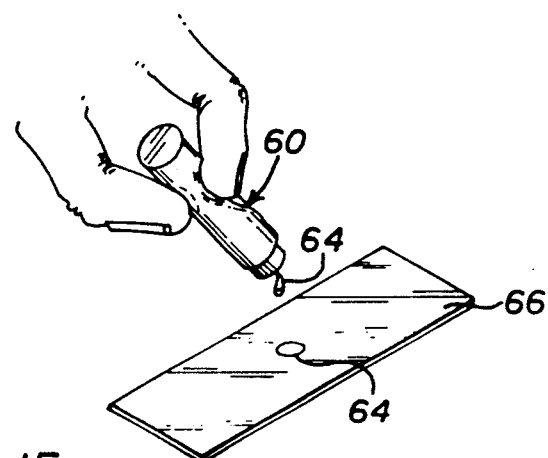
FIG. 15 is a perspective view showing expression of fluid from the auxiliary dropper cartridge.
Figure 16:
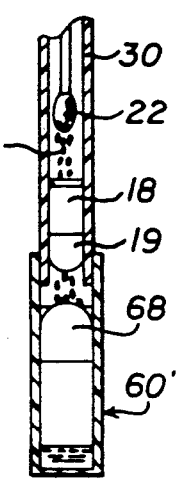
FIG. 16 is a fragmented sectional view illustrating an alternative configuration for the auxiliary dropper cartridge.

The invention can also be adapted for use with an auxiliary droplet cartridge 60 by insetting the filter plugs 18 and 19 a short distance from the outboard end 30' of the cap 30, as viewed in FIGS. 13 and 14. This permits the cap outboard end 30' to seat snugly and in substantially sealed relation into the open end of the cylindrical cartridge 60 having a drop former 62 of conventional design received therein. Still another reagent may be placed within the cartridge 60, if desired. The thus-modified unit can then be used to express the droplets 58 through the filter plugs 18 and 19 and further through the drop former 62 for mixture with the reagent in the cartridge 60. The mixed specimen and reagents can then be expressed in turn from the cartridge 60 in discrete droplets 64 onto a slide 66 or the like for further analysis, as shown in FIG. 15. Alternately, a modified cartridge 60' may include another porous filter member or plug 68 as the drop former structure, as viewed in FIG. 16.

Figure 17:
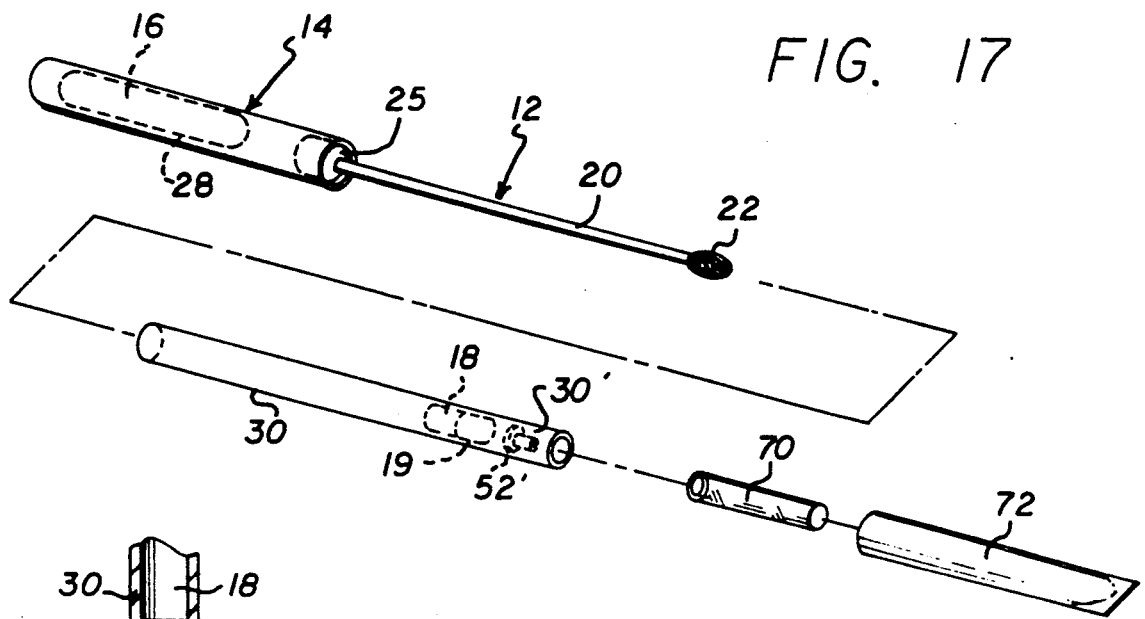
FIG. 17 is an exploded perspective view showing another alternative construction of a specimen test unit formed in accordance with the invention.
Figure 18:
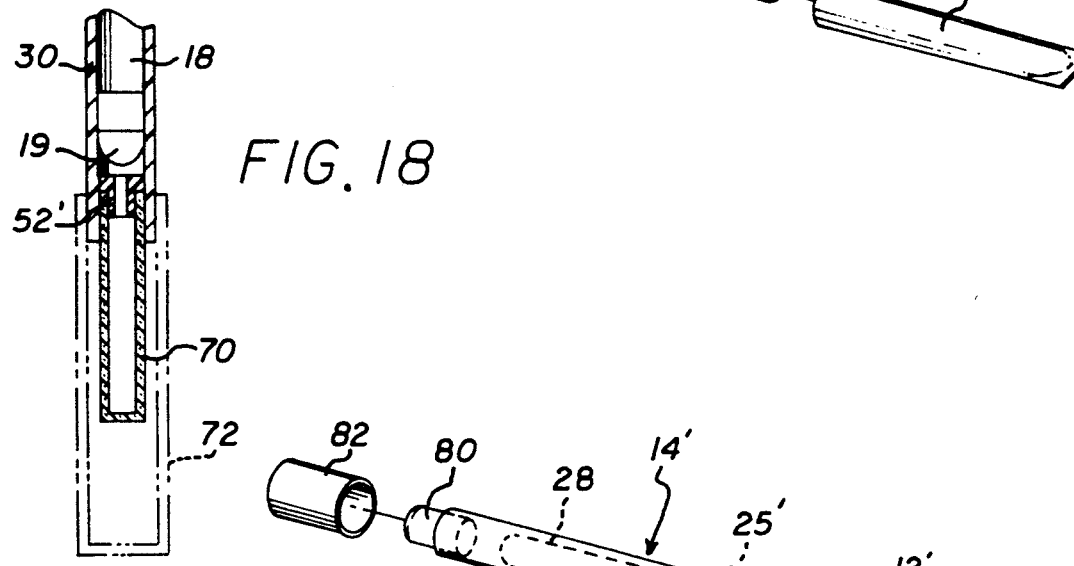
FIG. 18 is an enlarged fragmented vertical sectional view of a portion of the embodiment of FIG. 17 to depict use thereof in handling and processing a collected biological specimen.
Figure 19:
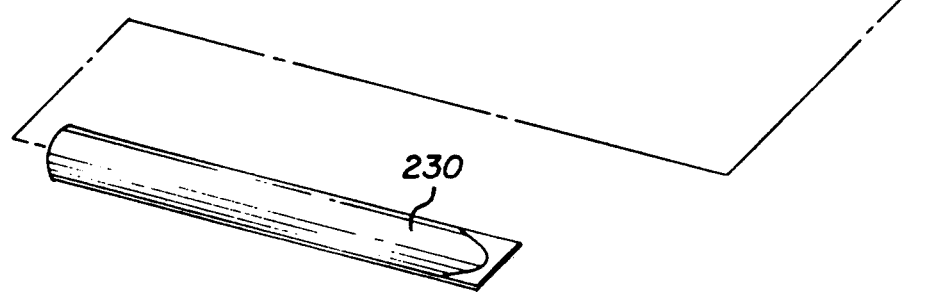
FIG. 19 is another exploded perspective view showing still another alternative configuration of the invention.
Figure 20:
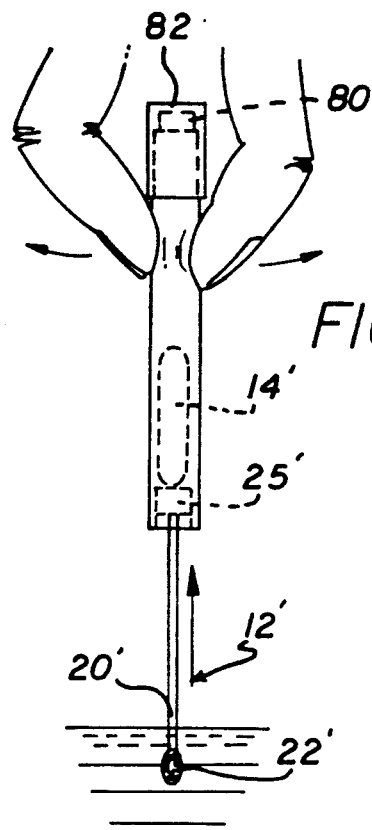
FIG. 20 is a side elevational view showing use of the embodiment of FIG. 19 for drawing a liquid or liquid-containing specimen for test purposes.

A further modified form of the invention is shown in FIGS. 17 and 18, wherein components identical to previously described embodiments are again designated by the same reference numerals. In this version, the base 14 again contains a reagent 16 or other test fluid within a rupturable ampoule 28 for expressed delivery through a porous plug member 25 to a swab member 12 or the like having, for example, a shank 20 and absorbent tip 22. A cylindrical cap 30 of open-ended construction is provided for mounting onto the base 14 to enclose and protect the swab member 12, and includes an outboard end 30' with one or more axially inset porous filter members, such as the illustrative plugs 18 and 19.

As shown best in FIG. 18, the outboard end 30, of the cap 30 also carries a small seal ring 52' which may be similar in construction to the seal ring 52 shown and described with respect to FIG. 11. The seal ring 52', however, is adapted for normal sealed engagement and friction fit with the open upper end of a small glass vial 70 or the like. An outer end cap 72 is normally provided for mounting onto the outboard end 30, of the cap 30 to cover and protect the glass vial 70. In a normal construction, the end cap 72 and the cap 30 will be formed from plastic material.

In use of the embodiment of FIGS. 17 and 18, a specimen will be collected as previously described herein and then contacted with one or more reagents by appropriate delivery of the test fluid 16 from the housing base 14 to contact the swab tip 22. The mixed specimen and reagent can then be delivered from the cap 30 by expression through the filter members 18 and 19, again as previously described. In this version, however, the mixed specimen and reagent are delivered into the glass vial 70. The glass vial 70 can then be placed into an appropriate optical detection device or the like for reading, for example, selected parameters of the mixed specimen/test fluid such as turbidity, color, etc. Importantly, the glass vial 70 can be placed into the optical detection device without requiring the vial to be touched by human hands, by removing the end cap 72 and placing the remainder of the test unit into an examination station of the optical detection device. This procedure advantageously isolates the vial from fingerprints, etc., which could adversely affect test read-out, and also safeguards against human contact with the specimen and reagents. Alternately, if desired, the glass vial can be separated from the cap 30 by squeezing inwardly on the end cap 72 to grasp and remove both components simultaneously from the cap 30.

A further modified form of the invention is shown in FIGS. 19–22, wherein this form of the invention is designed to express mixed specimen and reagent from the end of a housing base 14' opposite a supported swab member 12'. More specifically, with reference to FIG. 19, the modified housing base 14' is open-ended in construction with a hollow support member 25' at one end cooperating with a porous filter member 80 at the opposite end to retain a reagent containing ampoule 28 or the like within the housing member. A hollow tube swab shank 20' has an upper end communicating through the support member 25' and a lower end carrying a porous, absorbent tip 22'. An elongated cap 230 is adapted to fit with one end of the base 14' over the swab member 12', and a shorter end cap 82 is adapted to fit over the porous filter member 80 at the other end of the housing member.

Figure 22:
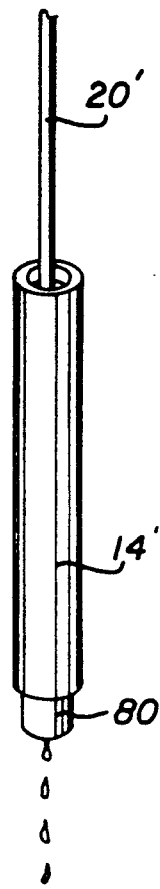
FIG. 22 is a perspective view illustrating delivery of a collected specimen and reagent from the embodiment of FIG. 19.
Figure 21:
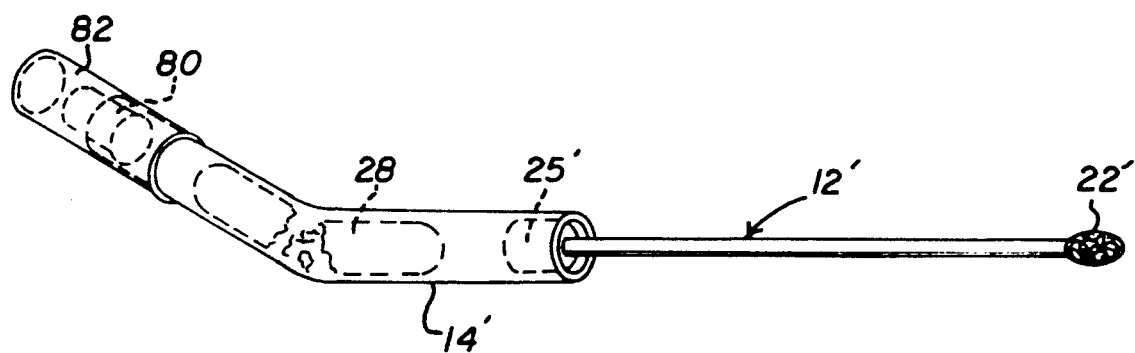
FIG. 21 is a perspective view illustrating release of a reagent for contacting the collected specimen, using the embodiment of FIG. 19.

In use, the elongated cap 230 is removed from the swab member 12' to permit a liquid specimen or liquid-carried specimen to be drawn by suction through the swab shank 20' into the interior of the base 14'. During this drawing step, as viewed in FIG. 20, the flexible plastic walls of the base 14' are first squeezed inwardly and then released to draw the specimen, with the specimen initially passing through the swab tip 22' for filtering purposes. The ampoule 28 can then be ruptured to release the reagent therein, as viewed in FIG. 21, followed by inversion of the base 14' to permit expression of the mixed specimen and reagent therein through the porous filter member 80, as shown in FIG. 22, upon appropriate inward squeezing of the side walls of the base 14'.

FIG. 23 shows still another modified embodiment of the invention wherein components which are identical in structure or function to those previously described are identified by common reference numerals. As shown in FIG. 23, an open-ended tubular housing base 14 is adapted to telescopically interfit with an open-ended housing cap 30 to cooperatively define a specimen chamber 31. A swab member 12 has a size and shape to to fit entirely within the specimen chamber 31 when the two housing members 14 and 30 are interconnected, with the swab member 12 being shown as a separate component unconnected to any other component of the test unit. The swab member 12 is utilized as previously described to collect a selected specimen on a swab tip 22 or the like, after which the swab with specimen thereon is dropped into the specimen chamber 31. The specimen chamber 31 is closed by interconnecting the housing members 14 and 30.

A selected reagent is delivered to the specimen chamber 31 to contact the collected specimen on the swab tip 22 and thus form a pool 56 of mixed specimen and reagent. FIG. 23 shows the reagent retained initially within a reagent chamber 26 defined cooperatively by the base 14 and a porous plug 25 inserted into the open end of the base 14. A frangible ampoule 28 may also be used to contain the reagent prior to a test procedure at which time the ampoule 28 is fractured to permit forcible delivery of the reagent through the porous plug 25 to the specimen chamber 31 all in a manner as previously described. Alternately, as shown in FIG. 24, the reagent chamber 26 can be omitted from the base 14, in which case the reagent can be added to the specimen chamber 31 by means of a separate dropper unit (not shown) or the like before the housing members 14 and 30 are interfitted with each other.

The cap 30 defines an outlet port 33 at its end opposite to the base 14. The outlet port 33 is sized for secure connection by press-fit reception of an occluding member 35 shown in FIGS. 23 and 24 to have a small flow orifice 37 formed therein. The size and geometry of the orifice 37 are chosen to prevent unforced liquid outflow from the specimen chamber 31, yet permit such outflow under pressure forced conditions. With this construction, the specimen and reagent will remain together within the specimen chamber 31 for a prescribed holding or incubation period, yet transfer quickly and easily to the exterior for further test or analysis when desired. Pressure forced flow of the mixed specimen and reagent through the orifice 37 can be obtained by manually squeezing one or both of the interfitted housing members 14 and 30 to increase the internal pressure within the specimen chamber 31. A closure cap 21 can be fitted over the occluding member 35 to insure positive closure of the orifice 37 unless and until liquid outflow is desired.

Further modified forms of the invention are shown in FIG. 25 and 26 wherein one or more auxiliary housing members of resilient plastic construction or the like are provided to pressure force mixed specimen and reagent from a specimen chamber 31 by vacuum draw. More particularly, FIG. 25 shows a specimen test unit constructed predominantly in accordance with FIG. 12 to include an interfitting housing base 14 and cap 30 defining a specimen chamber 31 for receiving a swab member 12 with collected specimen thereon. Although FIG. 25 shows the swab member 12 anchored in a seal ring 52 on the base 14, in combination with a reagent-containing ampoule 28, it will be understood that the test unit may be constructed according to any of the alternative embodiments described herein. The reagent is delivered to the specimen chamber 31 for contacting the specimen, thereby providing the mixture pool 56. An occluding member 35 mounted within an outlet port 33 on the cap 30 defines an internal orifice to prevent unforced flow of the liquid pool from the specimen chamber.

An open-ended auxiliary housing member 39 of molded plastic or the like is sized and shaped for press-on sealed fit onto the lower end of the cap 30. In this position, the auxiliary housing member 39 encloses the outlet port 33 and the occluding member 35 installed therein, as well as a small bore flow tube 41 projecting downwardly from the occluding member 35. A strip-shaped wick element 43 is loosely carried within the auxiliary housing member.

Manual depression of the auxiliary housing member 39 to squeeze the walls of the plastic structure, followed by release thereof, functions to vacuum draw a portion of the mixed specimen and reagent from the specimen chamber 31 through the occluding member 35 and the flow tube 41. A portion 56, of the liquid pool 56 is thus transferred to the bottom of the auxiliary housing member 39 where it contacts the wick element 43. The transferred liquid is drawn or wicked upwardly within the wick element 43, which may be impregnated with a reagent or the like for providing a final test result visual indicator.

FIG. 26 depicts an embodiment similar to FIG. 25, except that a pair of auxiliary housing members 39' and 39" are provided in series for two stage vacuum draw of a portion of the mixed specimen and reagent from the specimen chamber 31. The first auxiliary member 39' is equipped with an occluding member 35 similar to the one used at the cap outlet port 33. The second or lower auxiliary member 39" contains the wick element 43, and the associated flow tube 41 (FIG. 25) is omitted. In this version, the housing members 39' and 39" can be squeezed and released in sequence to draw the liquid from the specimen chamber 31 in two steps or stages. The lower housing member 39" can draw the fluid into contact with an upper edge of the wick element 43, with a controlled and timed liquid flow proceeding thereafter due to wicking action, without further pressure inducement.

FIGS. 27 and 28 depict a further modified embodiment similar to FIG. 25, but wherein the strip-shaped wick element 43 is supported directly from the occluding member 35. More particularly, the mixed specimen and reagent pool 56 within the specimen chamber 31 at the end of the cap 30 is blocked against unrestricted outflow from the specimen chamber 31 by the occluding member 35 having a small bore orifice or outlet port formed therein. In this embodiment, the orifice or outlet port in the occluding member 35 is open to an upper edge of the wick element 43, such that a slow capillary flow of mixed specimen and reagent to the wick element occurs immediately and without requiring pressure-forced fluid flow by positive pressure or vacuum draw action. Importantly, the cross sectional size and geometry of the wick element 43 are chosen to provide a regulated capillary flow, especially with respect to timing the flow rate so that the liquid contacts a reagent 16 on the wick element at a predetermined time subsequent to forming the mixed reagent-specimen pool 56.

FIGS. 29-32 depict still another modified form of the invention, wherein the specimen test unit includes a modified cap 330 which can be economically formed by blow molding or the like to include multiple internal chambers and an integral occluding member 135 with a small outflow port or orifice 137 formed therein. In this embodiment, the cap 330 is shaped to define a generally central restriction 332 adapted for slide-through passage of a swab 12 for placement of a collected specimen into a specimen chamber 331. One or more selected reagents can be delivered to the specimen chamber 331 in a manner described previously herein, to form a mixed specimen and reagent pool 356. An outlet port 337 leads from the specimen chamber 331 to a secondary mixing chamber 331', from which the mixed specimen and reagent can be dispensed through the port 137 to the exterior of the test unit. Both outlet ports 337 and 137 are sized to normally occlude fluid flow, while permitting pressure-forced fluid flow.

More particularly, a portion of the specimen-reagent pool 356 can be delivered quickly and easily through the outlet port 337 to the mixing chamber 331' by squeezing the cap to deformably compress the volume of the specimen chamber 331. The restrictor 332 prevents unrestricted liquid backflow within the cap during such squeeze motion to insure liquid delivery to the mixing chamber 331'. Alternately, the cap 330 can be squeezed in the region of the mixing chamber 331' to compress the volume thereof, followed by release to permit the cap material to expand and thereby vacuum draw the specimen and reagent to the mixing chamber 331'.

In accordance with one aspect of the embodiment of FIGS. 29-32, the volumetric capacity of the mixing chamber 331' can be accurately predetermined to permit chamber filling with a metered quantity of fluid. As shown in FIG. 32, the cap 330 includes a flat web 334 having the mixing chamber 331' and the outlet port 337 formed therein, such that the cap can be bent relatively easily at a point between the chambers 331 and 331' to occlude the intervening port 337. When the cap is bent in this manner, subsequent squeezing of the cap to compress the mixing chamber 331' is effective to dispense the metered chamber contents through the port 137 to the exterior of the test unit.

In another and/or alternative aspect of the embodiment of FIGS. 29-32, the mixed specimen and reagent pool 356 can be transferred back and forth between the two chambers 331 and 331', through the intervening port 337, by squeezing the cap in a manner alternately compressing the chambers. Such back and forth fluid transfer, conducted with a cap 31 closing the outlet port 337, beneficially breaks up cellular clusters or organisms which embody the desired specimen but which otherwise are not sufficiently or uniformly dispensed within the liquid pool 356. Thorough dispersal of the such organisms is effective and desirable to maximize reliability of a particular test to be performed.

The specimen test unit of the present invention thus provides a variety of different configurations each incorporating one or more porous plug or occlusion members through which liquid specimen and/or reagents or the like may be expressed. These occluding members provide simple yet highly effective means for filtering particulate matter from reagents and/or from a specimen, as required by the test to be performed. The test results can be read directly, for example, by observing colormetric changes or the like at various locations such as on any one of the porous filter or wick members or on the swab member, or by depositing mixed reagent and specimen onto a slide or the like for further analysis.

As one illustrative example of use of the invention, direct antigen testing can be performed quickly and easily, and in a manner which minimizes opportunity of exposure of testing personnel to the targeted organism and/or to the reagents used. One such direct antigen test in known for detecting Strep A, wherein the swab member can be used to collect a specimen which is then contacted with an appropriate succession of reagents and filtered to yield a colormetric indication located, for example, on a surface of one of the porous filter members. Of course, a wide range of different tests may be performed, with the invention providing a highly convenient, self-contained kit for safe specimen handling and prolonged storage of the appropriate reagents.

A variety of further modifications and improvements to the specimen test unit will be apparent to those skilled in the art. For example, in one form, the porous filter member can be formed simultaneously and integrally with the encasing housing member or the like, with the filter member having blown characteristics including the desired porous construction not present in the housing member. Accordingly, no limitation on the invention is intended by way of the description herein and the accompanying drawings, except as set forth in the appended claims.

What is claimed is:

1. A specimen test unit for use in collection and analysis of a biological specimen, said test unit comprising:
   an elongated, generally hollow housing member having open opposite ends;
   an occluding member having at least one flow orifice formed therein and disposed generally at a first end of said housing member;

a specimen collector having means for collecting a specimen and having a size and shape for collecting a specimen and having a size and shape for placement with the specimen into said housing member via a second end of said housing member, said housing member being adapted to receive at least one reagent;

a base member for mounting onto said second end of said housing member subsequent to placement of said specimen collector with the specimen into said housing member, said base member cooperating with said housing member and said occluding member to define a substantially closed specimen chamber having said specimen collector and specimen and reagent therein;

said flow orifice of said occluding member having a sufficiently small size for preventing unforced flow of the specimen and reagent within said specimen chamber, said flow orifice permitting pressure forced flow of the specimen and reagent from said specimen chamber to an exterior of said housing member; and vacuum drawing means operatively and removably connected to said flow orifice for vacuum drawing a portion of the specimen and reagent from said specimen chamber through said flow orifice to the exterior of said housing member.

2. The specimen test unit of claim 1 further including a cap mounted removably over said occluding member to close said flow orifice.

3. The specimen test unit of claim 1 wherein said housing member is formed at least in part from a resilient material to permit manual squeezing thereof to increase the relative pressure within said specimen chamber and thereby pressure force a portion of the specimen and reagent within said specimen chamber to flow through said flow orifice.

4. The specimen test unit of claim 1 wherein said base member has an elongated hollow construction with an open end and a closed end, said base member open end being slidably and telescopically engageable with said second end of said housing member for mounting said base member onto said housing member.

5. The specimen test unit of claim 4 wherein at least one of said housing member and said base member has at least a portion thereof formed from a resilient material to permit manual squeezing thereof to increase relative pressure within said specimen chamber and thereby pressure force a portion of the specimen and reagent within said specimen chamber to flow through said flow orifice.

6. The specimen test unit of claim 1 wherein said specimen collector comprises a swab member.

7. The specimen test unit of claim 6 wherein said swab member is mounted on said base member for placement into said housing member when said base member is mounted onto said housing member second end.

8. The specimen test unit of claim 1 wherein said base member is removably mounted onto said housing member.

9. The specimen test unit of claim 4 wherein said base member includes means for carrying the reagent and for delivering the reagent to said specimen chamber when said base member is mounted onto said housing member second end.

10. The specimen test unit of claim 1 wherein said vacuum drawing means comprises a vacuum housing mounted over and covering said flow orifice in said occluding member, said vacuum housing being manually deformable to vacuum draw a portion of the specimen and reagent through said flow orifice into said vacuum housing.

11. The specimen test unit of claim 10 wherein said vacuum housing is removably mounted onto said housing member.

12. The specimen test unit of claim 10 wherein said vacuum housing includes at least one resilient wall portion to permit manual squeezing and release, thereby vacuum drawing the specimen and reagent through said flow orifice.

13. The specimen test unit of claim 10 wherein said vacuum housing has an elongated hollow shape with one open and one closed end, said open end being slidably and telescopically engageable with said first end of said housing member.

14. The specimen test unit of claim 10 further including a wick element within said vacuum housing.

15. The specimen test unit of claim 14 further including means for delivering the portion of the specimen and reagent drawn through said flow orifice to a selected end of said wick element.

16. The specimen test unit of claim 1 wherein said vacuum drawing means comprises a first vacuum housing mounted over and covering said flow orifice in said occluding member, said first vacuum housing being manually deformable to vacuum draw a portion of the specimen and reagent through said flow orifice and into said first vacuum housing, and a second vacuum housing mounted onto said first vacuum housing and being manually deformable to vacuum draw a portion of the specimen and reagent from said first vacuum housing into said second vacuum housing.

17. A specimen test unit for use in collection and analysis of a biological specimen, said test unit comprising:

an elongated, generally hollow housing member having open opposite ends;

an occluding member having at least one flow orifice formed therein and disposed generally at a first end of said housing member;

a specimen collector having means for collecting a specimen and having a size and shape for placement with the specimen into said housing member via a second end of said housing member, said housing member being adapted to receive at least one reagent;

a base member for mounting onto said second end of said housing member subsequent to placement of said specimen collector with the specimen into said housing member, said base member cooperating with said housing member and said occluding member to define a substantially closed specimen chamber having said specimen specimen collector, specimen, and reagent therein;

said flow orifice of said occluding member having a sufficiently small size for preventing unforced flow of the specimen and reagent within said specimen chamber, said flow orifice permitting pressure forced flow of the specimen and reagent from said specimen chamber to the exterior of said housing member; and a secondary housing member mounted over and covering said flow orifice in said occluding member, said secondary housing member receiving the specimen and reagent upon flow thereof from said specimen chamber through said flow orifice; and a wick element within said secondary housing.

18. The specimen test unit of claim 17 further including means for delivering the specimen and reagent from said flow orifice to a selected end of said wick element, said means for delivering being located within said secondary housing member.

19. A specimen test unit for use in collection and analysis of a biological specimen, said test unit comprising:

an elongated, generally hollow housing member having open opposite ends;

an occluding member having at least one flow orifice formed therein and disposed generally at a first end of said housing member;

a specimen collector having means for collecting a specimen and having a size and shape for placement with the specimen into said housing member via a second end of said housing member, said housing member being adapted to receive at least one reagent;

a base member for mounting onto said second end of said housing member subsequent to placement of said specimen collector with the specimen into said housing member, said base member cooperating with said housing member and said occluding member to define a substantially closed specimen chamber having said specimen collector, and specimen, and reagent therein;

said flow orifice of said occluding member having a sufficiently small size for preventing unforced flow of the specimen and reagent within said specimen chamber, said flow orifice permitting pressure forced flow of the specimen and reagent from said specimen chamber to an exterior of said housing member; and a wick element having one end mounted within said flow orifice and projecting outwardly therefrom said wick element being positioned to contact the specimen and reagent within said specimen chamber for capillary flow thereof through said flow orifice to the exterior of said housing member.

20. The specimen test unit of claim 19 wherein said wick element has a reagent disposed at a determined position along the length thereof.

21. A specimen test unit for use in collection and analysis of a biological specimen, said test unit comprising:

an elongated, generally hollow housing member having open opposite ends;

an occluding member having at least one flow orifice formed therein and disposed generally at a first end of said housing member;

a specimen collector having means for collecting a specimen and having a size and shape for placement with the specimen into said housing member via a second end of said housing member, said housing member being adapted to receive at least one reagent;

a base member for mounting onto said second end of said housing member subsequent to placement of said specimen collector with the specimen into said housing member, said base member cooperating with said housing member and said occluding member to define a substantially closed specimen chamber having said specimen collector, and specimen, and reagent therein;

said flow orifice of said occluding member having a sufficiently small size for preventing unforced flow of the specimen and reagent within said specimen chamber, said flow orifice permitting pressure forced flow of the specimen and reagent from said specimen chamber to an exterior of said housing member; and said housing member further including means defining a mixing chamber, said flow orifice defining a first port leading from said mixing chamber to the exterior of said housing member, and further including means defining a second port communicating between said specimen and mixing chambers.

22. The specimen test unit of claim 21 wherein said housing member is deformable to permit manual compression of said specimen and mixing chambers, whereby the specimen and reagent are transferrable back and forth through said second port between the specimen and mixing chambers upon deformation of said housing member to alternately compress said specimen and mixing chambers.

23. The specimen test unit of claim 22 wherein said housing member is deformable at a position between said specimen and mixing chambers to occlude said second port whereby said housing member is further deformable to compress said mixing chamber to dispense specimen and reagent therein through said first port.

24. The specimen test unit of claim 23 wherein said housing member includes a web having said second port formed therein and extending between said specimen and mixing chambers.

* * * * *